US00RE36398E

United States Patent [19]

Byrne et al.

[11] E Patent Number: Re. 36,398

[45] **Reissued Date of Patent: *Nov. 16, 1999**

[54] SAFETY DEVICE FOR HYPODERMIC NEEDLE OR THE LIKE

[75] Inventors: Phillip O. Byrne; Penelope R. Seiders; Harry R. Ingham, all of Newcastle Upon Tyne, United Kingdom

[73] Assignee: BTG International Limited, United Kingdom

[ * ] Notice: This patent is subject to a terminal disclaimer.

[21] Appl. No.: 09/116,673

[22] Filed: Jul. 16, 1998

Related U.S. Patent Documents

Reissue of:

[64] Patent No.: 5,549,572
Issued: Aug. 27, 1996
Appl. No.: 08/435,396
Filed: May 5, 1995

[63] Continuation of application No. 08/160,859, Dec. 3, 1993, Pat. No. 5,601,535, which is a continuation of application No. 07/709,999, Jun. 4, 1991, abandoned, which is a continuation of application No. 07/595,664, Oct. 11, 1990, Pat. No. 5,084,030, which is a continuation of application No. 07/241,256, Sep. 7, 1988, abandoned, which is a continuation of application No. 06/888,376, Jul. 23, 1986, Pat. No. 4,826,490.

[30] Foreign Application Priority Data

Jul. 29, 1985 [GB] United Kingdom ..... 8519049

[51] Int. Cl.[6] ..... A61M 5/32

[52] U.S. Cl. ..... 604/198; 604/110; 604/263

[58] Field of Search ..... 604/110, 192, 604/198, 263

[56] References Cited

U.S. PATENT DOCUMENTS

| | | |
|---|---|---|
| Re. 27,797 | 10/1973 | Sorenson et al. . |
| 2,876,770 | 10/1959 | White . |
| 2,925,083 | 12/1960 | Craig . |
| 3,323,523 | 6/1967 | Scislowicz et al. . |
| 3,463,152 | 8/1969 | Sorenson . |
| 3,536,073 | 10/1970 | Farb . |
| 3,574,306 | 4/1971 | Alden . |
| 3,610,240 | 10/1971 | Harautuneian . |
| 3,658,061 | 4/1972 | Hall . |
| 3,884,230 | 5/1975 | Wulff . |
| 3,890,971 | 6/1975 | Leeson et al. . |
| 3,904,033 | 9/1975 | Haerr . |
| 4,170,993 | 10/1979 | Alvarez . |
| 4,425,120 | 1/1984 | Sampson et al. . |

(List continued on next page.)

FOREIGN PATENT DOCUMENTS

| | | |
|---|---|---|
| 2119148 | 7/1948 | Australia . |
| 201484 | 2/1955 | Australia . |
| 164214 | 3/1955 | Australia . |
| 202213 | 5/1955 | Australia . |
| 232255 | 9/1959 | Australia . |
| 253057 | 6/1963 | Australia . |
| 57556/69 | 2/1971 | Australia . |
| 13731/70 | 10/1971 | Australia . |
| 813433 | 7/1951 | Germany . |
| 49-4797 | 2/1974 | Japan . |
| 924734 | 5/1963 | United Kingdom . |
| 1233302 | 5/1971 | United Kingdom . |
| 1297746 | 11/1972 | United Kingdom . |
| 2059268 | 4/1981 | United Kingdom . |
| 2114006 | 8/1983 | United Kingdom . |

*Primary Examiner*—Corrine McDermott
*Attorney, Agent, or Firm*—Nixon & Vanderhye P.C.

[57] ABSTRACT

A safety device for a hypodermic needle or for a similar instrument used in the clinical puncture of the skin comprises a sheath (6, 25 or 32) adapted to be connected to the needle (5, 21 or 33) or to a support (4 or 31) for the needle. The sheath is so connected in a first position (FIGS. 1A, 2A, or 3A) which permits normal use of the needle and can be placed, by movement relative to the needle (FIGS. 1B or 3B) or by folding upon itself (FIGS. 2B and 2C) in a second position in which the needle is encapsulated by the sheath. The sheath is retained in that second position, for example by a projection (9, 27 or 35) extending into a slot (10 or 36) or through an aperture (28).

16 Claims, 4 Drawing Sheets

U.S. PATENT DOCUMENTS

| | | |
|---|---|---|
| 4,573,976 | 3/1986 | Sampson et al. . |
| 4,631,057 | 12/1986 | Mitchell . |
| 4,664,259 | 5/1987 | Landis . |
| 4,666,435 | 5/1987 | Bragintez . |
| 4,693,257 | 9/1987 | Markham . |
| 4,695,274 | 9/1987 | Fox . |
| 4,743,233 | 5/1988 | Schneider . |
| 4,826,490 | 5/1989 | Byrne et al. . |
| 4,931,048 | 6/1990 | Lopez et al. . |
| 5,084,030 | 1/1992 | Byrne et al. . |
| 5,120,320 | 6/1992 | Fayngold . |
| 5,348,544 | 9/1994 | Sweeney et al. . |
| 5,536,257 | 7/1996 | Byrne et al. . |
| 5,601,535 | 2/1997 | Byrne et al. . |

Fig. 2A *(AMENDED)*

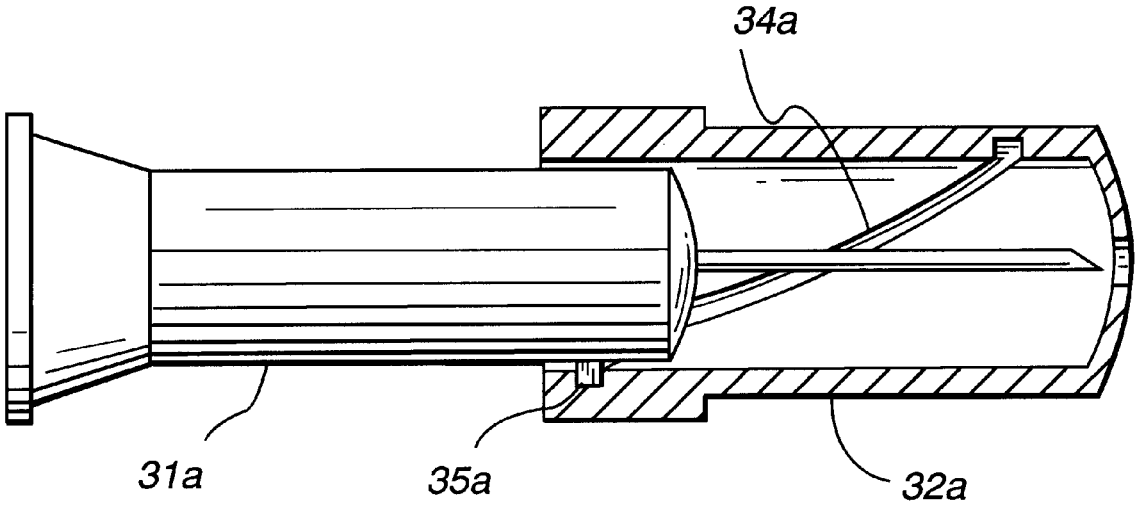
Fig. 6 *(NEW)*

SAFETY DEVICE FOR HYPODERMIC NEEDLE OR THE LIKE

Matter enclosed in heavy brackets [ ] appears in the original patent but forms no part of this reissue specification; matter printed in italics indicates the additions made by reissue.

This is a continuation of Ser. No. 08/160,859 filed Dec. 3, 1993 (*now U.S. Pat. No. 5,601,535*), which is a continuation of Ser. No. 07/709,999 filed Jun. 4, 1991 (*now abandoned*), which a continuation of Ser. No. 07/595,664 filed Oct. 11, 1990 (now U.S. Pat. No. 5,084,030), which is a continuation of 07/241,256 filed Sep. 7, 1988 (now abandoned), which is a continuation of Ser. No. 06/888,376 filed Jul. 23, 1986 (now U.S. Pat. No. 4,826,490).

The present invention is a safety device for a hypodermic needle or similar instrument used in the clinical puncture of the skin.

The taking of blood samples from persons in hospitals, health centres or other clinical areas is a routine medical procedure, as is the injection of pharmnaceutical preparations or biological materials. However, many incidents have been reported in the press and in medical journals of clinical operators subsequently accidentally wounding themselves or other persons with the needle and thereby either transmitting a disease or causing chemical or biological poisoning.

There is a clear need for a device which permits the disposal of a hypodermic needle or such instrument in a manner which protects the clinical operator, observers of the clinical procedure and all other persons concerned, including the general public, from accidental wounding.

It is an object of the present invention to provide such a device.

The safety device according to the invention for a hypodermic needle or similar instrument comprises a sheath, adapted to be connected to said needle or other instrument or to a support therefor in a first position which permits normal use of said needle or other instrument and to be placeable, by movement relative to the needle or other instrument or by folding upon itself, in a second position in which the needle or other instrument is encapsulated by the sheath and the sheath is retained in that second position.

As indicated, the safety device of the present invention is generally applicable to the protection of puncturing instruments typified by hypodermic needles, although among such instruments hypodermic needles are by far the most widely used. For example, the device may be applied to the protection of biopsy needles, winged needles, that is needles provided with lateral attachments to enable them to be affixed to the skin surface as by adhesive tape, and to intravenous cannulas and lumbar puncture needles. For convenience, the invention is hereinafter described specifically as applied to "needles", in particular hypodermic needles, but it is emphasised that the invention is not to be limited thereby.

The sheath is adapted to be attached to the needle or to a support for the needle but may be provided separately from the needle, to be attached to the needle or support at the point of use, either before or after the needle has actually been used It is much preferred that such separate sheaths be attached before use, so that the needle may be more readily encapsulated immediately after it has been used. However, the sheath according to the present invention is preferably and conveniently supplied already attached to the needle. In particular, it is preferably attached either irremovably or in a way which makes its removal diificult. For example, the sheath may be adhered to the needle or to a support for the needle or may be clipped to the needle or support.

When the needle is designed for use without a syringe or remote from an associated syringe, to which it is then linked by a flexible tube, then the sheath is preferably secured direct to the needle. The sheath may then conveniently incorporate one or more parts which are foldable relative to the body of the sheath and thereby to encapsulate the needle.

When the needle, on the other hand, is mounted upon a housing designed to be attached to a syringe barrel or luer connector, then the sheath may advantageously be secured to the housing. The sheath may then be capable of movement relative to the housing in a direction which has a component parallel to the length of the needle, so that the sheath may be moved along the length of the needle until the latter is fully encapsulated. This relative movement of sheath and housing may for example be a linear sliding movement or a spiral movement, as more particularly exemplified hereinafter in FIGS. [3A] *2A* and [3B] *5A* of the drawings.

Such relative movement of sheath and housing may be determined by one or more linear or spiral grooves or channels in the housing engaging one or more lugs or other projections on the sheath—or grooves or channels in the sheath engaging projections on the housing.

In the second position of the sheath, in which the needle is encapsulated, the sheath is retained against further movement relative to the needle. That retaining of the sheath is preferably irreversible or reversible only with difficulty. For example, one or more lugs or other projections on one of the relatively movable components may engage one or more apertures or slots in the other component, preferably under the pressure of a natural resilience in at least one of the components or under pressure from one or more springs.

The sheath may advantageously and conveniently be made from a resilient plastics material, for example polypropylene, and the housing may be made from the same, or a similar, material.

The invention will now be further described with reference to the accompanying drawings, wherein:

FIG. 2A is a view corresponding to that of FIG. 1A but with the sheath moved to encapsulate the needle;

Figure 5A:
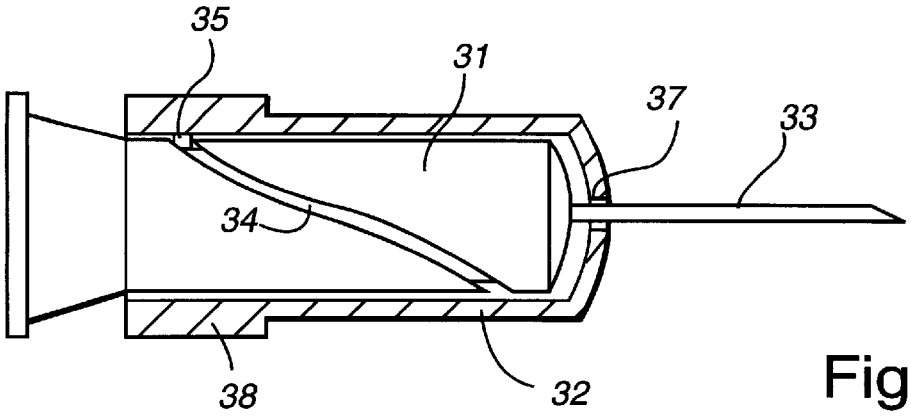
FIG. 5A is a view, partly in section of a third embodiment of the safety device according to the present invention, in a position in which the needle may be used normally.
Figure 5B:
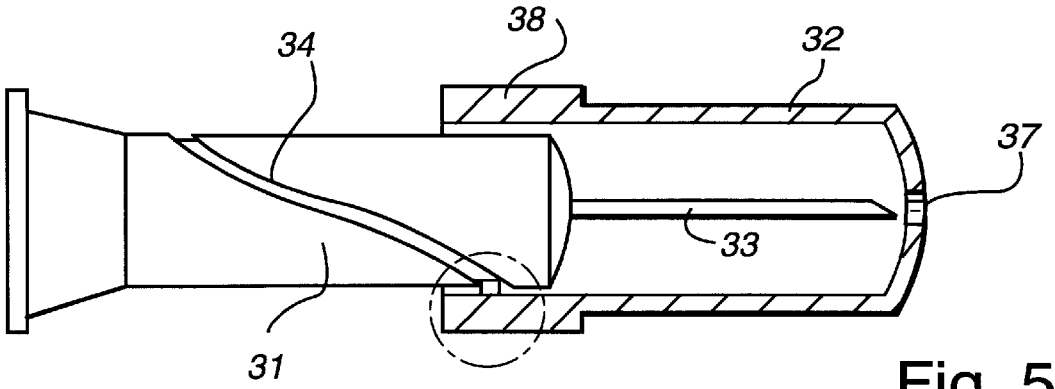
FIG. 5B is a view corresponding to that of FIG. 5A but with the sheath moved to encapsulate the needle.

*New FIG. 6 is a view similar to FIG. 5B illustrating a further form of the guide slot and projection.*

Figure 1A:
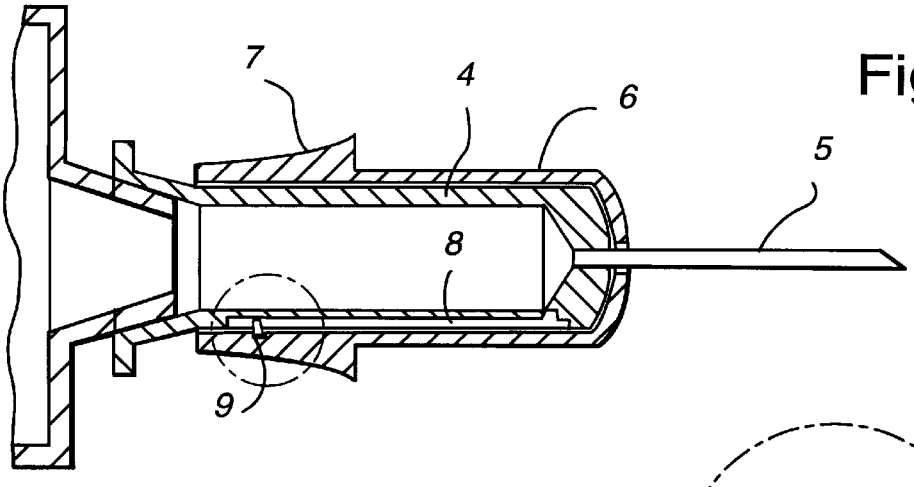
FIG. 1A is a sectional view of a first embodiment of the safety device according to the present invention, in a position in which the needle may be used normally.
Figure 1B:
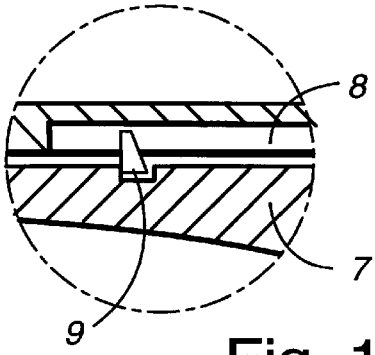
FIG. 1B is an enlarged detailed view of the circled portion of FIG. 1A.
Figure 2B:
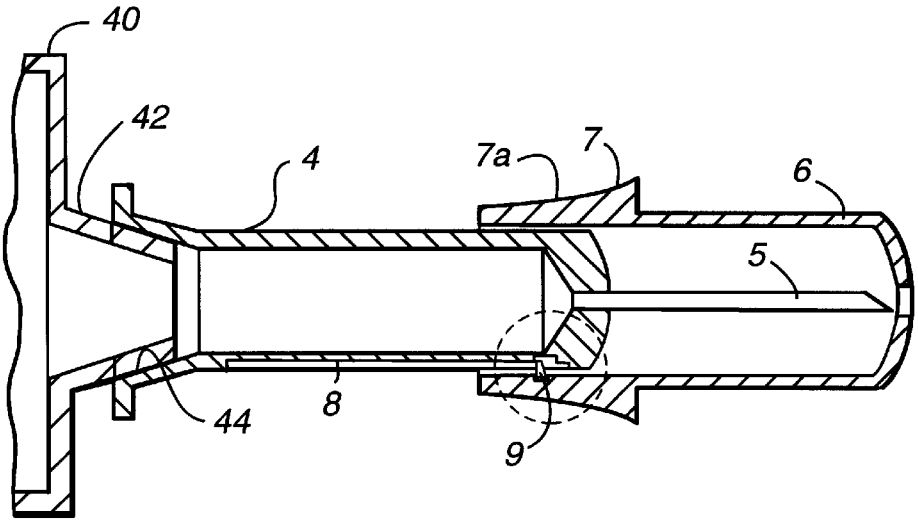
FIG. 2B is an enlarged detailed view of the circled portion of FIG. 2A.
Figure 2B:
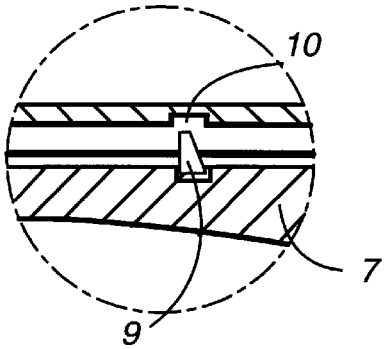
Figure 3:
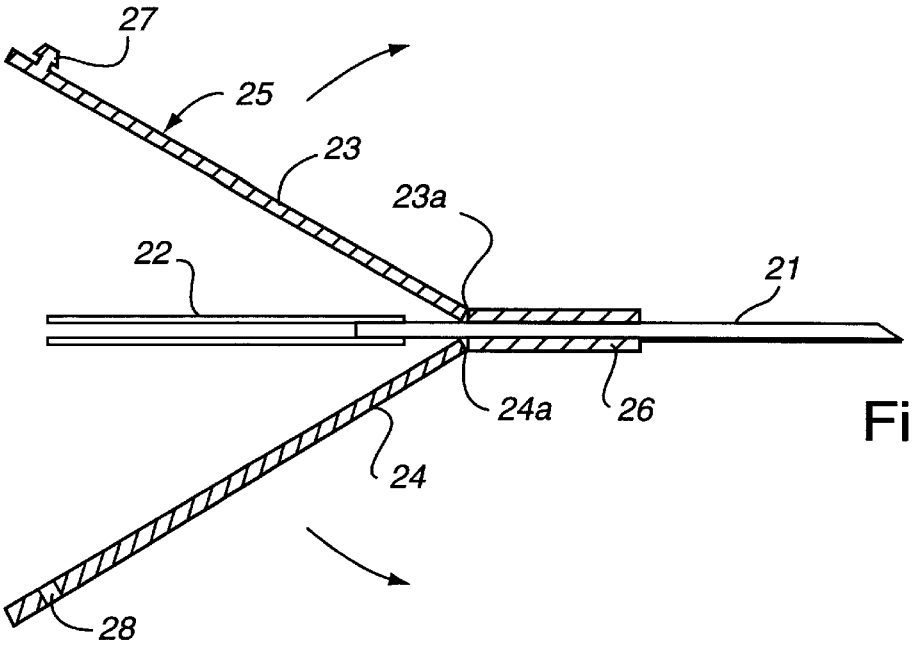
FIG. 3 is a sectional view of a second embodiment of the safety device according to the present invention, in a position in which the needle may be used normally.
Figure 4B:
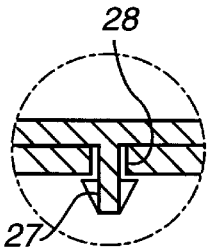
FIG. 4B is an enlarged view of the circled portion of FIG. 4A.
Figure 4A:
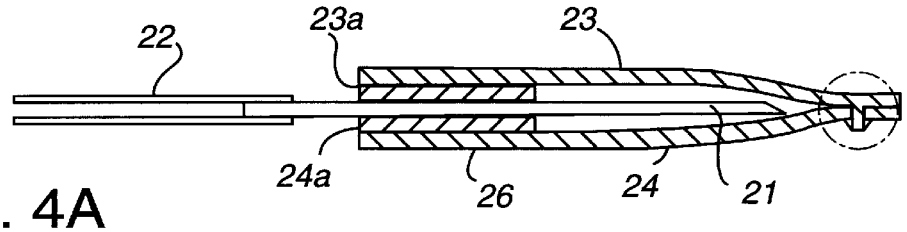
FIG. 4A is a view corresponding to that of FIG. 3 but with the sheath folded to encapsulate the needle.
Figure 4C:
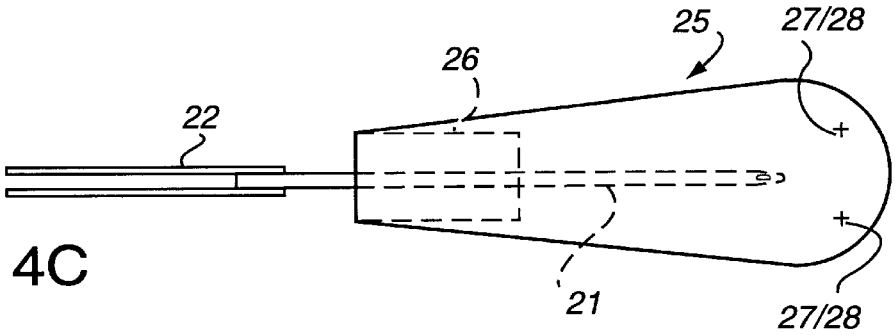
FIG. 4C is a plan view of the device in the position shown in FIG. 4A.

The embodiment of the invention shown in FIGS. 1A and 1B comprises a needle housing 4 in the form of a plastics moulding carrying a needle 5 and, slidably supported upon the housing 4, a plastics sheath 6 incorporating a thumb guard 7 integral therewith. *The thumb guard 7 constitutes a lateral enlargement of the guard and as illustrated in FIG. 2A has an arcuate surface 7a providing a finger-engaging surface. The needle housing 4 thus comprises a hollow support structure and forms with needle 5 a sub-assembly.* Also incorporated in the housing 4 and running length-wise, is a channel 8. The sheath 6 incorporates a self-springed spigot 9, which slides along the channel 8, as shown in more detail in the enlarged inset. When the sheath travels to the end of the channel 8, the self-springed spigot 9 drops into a small "well" 10, thus locking the sliding sheath in position. The length of the sheath is such that, when it is locked in position, the sharp end of the needle is completely enclosed by the sheath, as shown in FIG. 1B.

The housing 4 is designed to mate with any standard syringe barrel or luer connector. After use, the protective sheath is extended into the locked position, thus encapsulating the needle in a safe manner.

The embodiment of the invention shown in FIGS. [2A to 2C] *3 and 4A–4C* is designed to allow encapsulation of a hypodermic needle 21 which is tethered to a syringe (not shown) by an extension tube 22. The needle 21 is sandwiched between two plastics mouldings or pressings 23,24 which together form a sheath 25. A part 26 of the sheath 25 is permanently attached to the hypodermic needle. At points 23a and 24a the plastic is formed in a manner which allows the free ends of members 23 and 24 to hinge as indicated Near to its outer end, the member 23 carries two spigots 27, which are designed to mate with holes 28 in the member 24 (when the sheath is in its folded position) and lock the sheath securely around the needle 21.

The third embodiment of the invention, as illustrated in FIGS. [5A and 5B] *5A–5C*, comprises a needle housing 31 in the form of a plastics moulding, a plastics sheath 32 which is free to rotate thereon and a needle 33. Impressed into the housing 31 is helical groove 34 extending from near the end of the housing 31 which is distal to the needle 33 towards the needle. The sheath 32 has a self-springed spigot 35 which fits into, and is free to move along, the helical groove 34 *while subject to a biasing force acting between the sheath 32 and housing 31 during relative movement of the sheath and housing*. As shown in FIG. [3B] *5B*, rotation of the sheath 32 in a clockwise direction (viewed from the rear) will result in a forward motion causing the sheath to encapsulate the needle 33. At the end of its travel the springed spigot 35 drops into a "well" 36 thereby locking the sheath in position. The length of the sheath 32 is such that when it has reached this locked position the needle is completely encapsulated and withdrawn beyond the orifice 37 in the outer end of the sheath.

The device shown in FIGS. [3A and 3B] *5A–5C* is designed to mate with any standard syringe barrel or luer connector. *For example, as illustrated in FIG. 2A, a connector formation is provided on an elongate body 40 including a tapered abutment surface 42 for mating with the needle support housing and having a complementary tapered abutment surface 44.* After use, the protective sheath is placed in position by applying a twisting force to the sheath. To facilitate the application of this twisting force, a raised section 38 may be incorporated into the sheath's surface.

This form of the invention may be fabricated with one or more helical grooves, which may extend in a clockwise or anti-clockwise direction. For greater mechanical strength and stability, a double helix may be preferred.

Figure 5C:
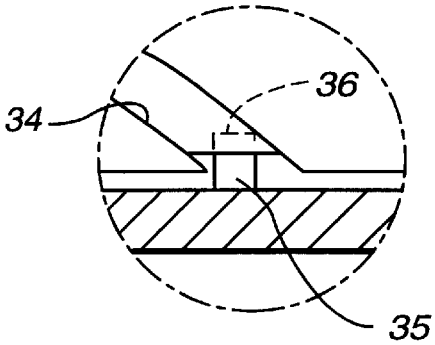
FIG. 5C is an enlarged view of the circled portion of FIG. 5B[.] *;*

*In FIG. 6, the groove 34a and spigot 35a are formed in the sheath 32a and housing 31a, respectively, i.e., reversed as previously described from the configuration of FIGS. 5A–5C.*

We claim:

1. For use with clinical apparatus operably applicable to a patient by way of a deliberate skin puncture, a needle assembly operable to effect said skin puncture and comprising:

a support structure;

a needle fixedly mounted in said structure to form therewith a sub-assembly, with one end portion of said needle projecting from said structure, and said one end portion terminating in a skin-puncturing tip;

a guard mounted around part of said sub-assembly for movement relative thereto in the longitudinal direction of said needle from a first position in which said tip is exposed to effect said deliberate puncture, to a second position in which said tip is embraced by said guard to prevent unintended skin puncture;

a locking mechanism including first and second elements, said first element being a projection from one of said sub-assembly and guard, said second element being a stop surface defining a space bordering the other of said sub-assembly and guard, said elements each extending transversely of said needle longitudinal direction, said elements being spaced apart in said longitudinal direction when said guard is in said first position, said projection being subject to a bias force acting between said sub-assembly and guard during said relative movement, and said projection being automatically irreversibly moved into said space alongside said stop surface in response to said bias force when said guard is in said second position to inhibit a returning relative movement thereof towards said first position; and a stop mechanism effective to constrain said guard from movement towards and around said apparatus.

2. An assembly according to claim 1 wherein said locking mechanism second element stop surface defines said space as a recess in the other of said sub-assembly and guard.

3. An assembly according to claim 1 wherein, to serve as said stop mechanism, said support structure has a portion with external dimensions transversely of said longitudinal direction which are enlarged relative to the remainder of the structure, and said guard has lesser corresponding internal transverse dimensions around said structure than said portion.

4. For use with clinical apparatus operably applicable to a patient by way of a deliberate skin puncture, a needle assembly operable to effect said skin puncture and comprising:

a support structure;

a needle fixedly mounted in said structure to form therewith a sub-assembly, with one end portion of said needle projecting from said structure, and said one end portion terminating in a skin-puncturing tip;

a guard mounted around part of said sub-assembly for movement relative thereto in the longitudinal direction of said needle from a first position in which said tip is exposed to effect said deliberate puncture, to a second position in which said tip is embraced by said guard to prevent unintended skin puncture;

a locking mechanism including first and second elements, said first element being a projection from one of said sub-assembly and guard, said second element being a stop surface defining a space bordering the other of said sub-assembly and guard, said elements each extending transversely of said needle longitudinal direction, said elements being spaced apart in said longitudinal direction when said guard is in said first position, said projection being subject to a bias force acting between said sub-assembly and guard during said relative movement, and said projection being automatically irreversibly moved into said space alongside said stop surface in response to said bias force when said guard is in said second position to inhibit a returning relative movement thereof towards said first position;

a stop mechanism effective to constrain said guard from movement towards and around said apparatus;

said stop mechanism including a portion of said support structure having external dimensions transversely of said longitudinal direction which are enlarged relative to the remainder of the structure, and said guard having lesser corresponding internal transverse dimensions around said structure than said portion;

said support structure having a connector formation for removable attachment with said clinical apparatus, which formation includes said transversely enlarged portion.

*5. For use with clinical apparatus operably applicable to a patient by way of a deliberate skin puncture, a needle assembly operable to effect said skin puncture and comprising:*

*a hollow support structure;*

*a needle fixedly mounted on said structure adjacent one end thereof to form therewith a sub-assembly, with one end portion of said needle projecting from said structure, and said one end portion terminating in a skin puncturing tip having an opening therein, the needle being longitudinal hollow to provide a direct fluid flow pathway extending therethrough between said opening in said tip and the remainder of said needle from said one end portion, the needle having no obstruction therein along the entire length of said pathway so that direct fluid flow along the entire length of the pathway is permitted;*

*said support structure including a connector formation at an opposite end thereof from said needle to engage, in use of said needle assembly, with the clinical apparatus, said connector formation being integral with said support structure and having an opening therethrough in communication through said support structure with said pathway through said needle;*

*a guard mounted for movement relative to said sub-assembly and in a longitudinal direction of said needle between a first position in which said tip is exposed to effect said deliberate skin puncture and a second position in which said guard extends in part longitudinally beyond said tip to prevent unintended skin puncture;*

*said guard being carried by said sub-assembly in a captive manner to stop separation of said guard from said sub-assembly by movement from said first position in the longitudinal direction away from said second position;*

*a projection carried by said guard and projecting generally laterally of the longitudinal direction of said needle, said projection engaging said sub-assembly during said relative movement of said guard and said sub-assembly from said first position towards said second position;*

*said projection being subject to a biasing force acting between said guard and part of said sub-assembly during said relative movement of said guard and said sub-assembly;*

*said projection being automatically displaced in a general lateral direction in response to said relative movement of said guard and said sub-assembly to lock said guard and said sub-assembly in said second position.*

*6. An assembly according to claim 5 wherein said sub-assembly includes a guide for guiding said projection along said sub-assembly and throughout the extent of said relative movement of said guard and said sub-assembly from said first position to said second position.*

*7. An assembly according to claim 6 wherein said guide includes a groove formed in said sub-assembly.*

*8. An assembly according to claim 5 wherein said projection is subject to said biasing force throughout the extent of said relative movement of said guard and said sub-assembly from said first position to said second position.*

*9. An assembly according to claim 5 wherein said projection engages said sub-assembly in said second position of said guard and said sub-assembly.*

*10. An assembly according to claim 5 wherein said projection is subject to said biasing force throughout the extent of said relative movement of said guard and said sub-assembly from said first position to said second position, said projection engaging said sub-assembly in said second position of said guard and said sub-assembly.*

*11. For use with clinical apparatus operably applicable to a patient by way of a deliberate skin puncture, a needle assembly operable to effect said skin puncture and comprising:*

*an elongated support structure having first and second ends and a first direct fluid flow pathway between said ends, said first end adapted for connection and fluid communication with the clinical apparatus:*

*a needle fixedly mounted adjacent said second end of said structure to form therewith a sub-assembly, one end portion of said needle projecting from said structure and terminating in a skin puncturing tip having an opening therein, the needle being longitudinally hollow to provide a second direct fluid flow pathway extending therethrough between said opening in said tip and the remainder of said needle from said one end portion and in open communication with said first pathway to form a continuous direct fluid flow pathway between said support structure first end and said opening in said tip, the needle and said support structure having no obstruction therein along the entire length of said continuous pathway so that direct fluid flow along the entire length of said continuous pathway is permitted;*

*a guard mounted for movement relative to said sub-assembly and in a longitudinal direction of said needle between a first position in which said tin is exposed to effect said deliberate skin puncture and a second position in which said tip is enclosed by said guard to prevent unintended skin puncture;*

*said guard being carried by said sub-assembly in a captive manner to stop separation of said guard from said sub-assembly by movement from said first position in the longitudinal direction away from said second position;*

*a projection carried by one of said sub-assembly and said guard and projecting generally laterally of the longitudinal direction of said needle;*

*a guide slot extending along at least one side of another of said sub-assembly and said guard generally in the longitudinal direction of the needle and terminating at one end in a recess having a stop surface;*

*said projection engaging in said slot in said first position of said guard and said sub-assembly and engaging along said slot during said relative movement of said*

*guard and said sub-assembly from said first position to said second position;*

*said projection extending into said recess upon said relative movement of said guard and said sub-assembly into said second position and engageable against said stop surface to prevent relative movement of said guard and said sub-assembly from said second position toward said first position;*

*said guard in said second position extending in part longitudinally beyond said needle tip and enclosing said needle tip.*

*12. An assembly according to claim 11 including a lateral enlargement of said guard adjacent an end thereof remote from said needle in said second position of said guard.*

*13. An assembly according to claim 12 wherein said enlargement has an arcuate surface providing a finger-engaging surface.*

*14. An assembly according to claim 11 wherein said projection and said another of said guard and said sub-assembly are subject to a biasing force substantially throughout the extent of relative movement of said guard and said sub-assembly from said first position to said second position enabling said projection to engage said stop surface in said second position of said guard and said sub-assembly to prevent said movement from said second position toward said first position.*

*15. An assembly according to claim 11 wherein said guide slot is formed along said guard and said projection projects from said sub-assembly.*

*16. An assembly according to claim 11 wherein said guide slot is formed along said sub-assembly and said projection projects from said guard.*

* * * * *

UNITED STATES PATENT AND TRADEMARK OFFICE

CERTIFICATE OF CORRECTION

PATENT NO. Re. 36,398

DATED: November 16, 1999

INVENTORS: Byrne et al.

It is hereby certified that errors appear in the above-identified patent and that said Letters Patent is hereby corrected as shown below:

Claim 11: column 6, line 48, change "tin" to --tip--.

Signed and Sealed this

Eighth Day of May, 2001

*Attest:*

Nicholas P. Godici

NICHOLAS P. GODICI

*Attesting Officer*

*Acting Director of the United States Patent and Trademark Office*